(12) United States Patent
O'Donnell

(10) Patent No.: US 7,549,985 B2
(45) Date of Patent: Jun. 23, 2009

(54) METHOD AND SYSTEM TO CREATE AND ACOUSTICALLY MANIPULATE A MICROBUBBLE

(75) Inventor: Matthew O'Donnell, Ann Arbor, MI (US)

(73) Assignee: The Regents of the University of Michigan, Ann Arbor, MI (US)

(*) Notice: Subject to any disclaimer, the term of this patent is extended or adjusted under 35 U.S.C. 154(b) by 280 days.

(21) Appl. No.: 10/603,341

(22) Filed: Jun. 25, 2003

(65) Prior Publication Data

US 2004/0054357 A1    Mar. 18, 2004

Related U.S. Application Data

(60) Provisional application No. 60/392,318, filed on Jun. 26, 2002.

(51) Int. Cl.
*A61B 18/18*   (2006.01)
*G01N 3/00*    (2006.01)
*G01N 3/30*    (2006.01)
*G01N 7/00*    (2006.01)
*G01M 3/02*    (2006.01)

(52) U.S. Cl. .................. 606/10; 606/12; 73/12.07; 73/12.08; 73/37; 73/432.1

(58) Field of Classification Search .......... 601/2; 606/2, 4, 10–13; 73/12.07, 12.08, 37, 432.1
See application file for complete search history.

(56) References Cited

U.S. PATENT DOCUMENTS

| | | | |
|---|---|---|---|
| 5,615,675 A | 4/1997 | O'Donnell et al. | |
| 5,620,857 A | 4/1997 | Weetall et al. | |
| 5,732,046 A | 3/1998 | O'Donnell et al. | |
| 5,749,364 A | 5/1998 | Sliwa et al. | |
| 5,810,731 A | 9/1998 | Sarvazyan et al. | |
| 6,113,570 A * | 9/2000 | Siegel et al. | 601/2 |
| 6,146,375 A | 11/2000 | Juhasz et al. | |
| 6,165,440 A | 12/2000 | Esenaliev | |
| 6,391,020 B1 * | 5/2002 | Kurtz et al. | 606/2 |
| 6,416,190 B1 | 7/2002 | Grier et al. | |
| 6,471,968 B1 | 10/2002 | Baker et al. | |
| 6,546,272 B1 | 4/2003 | MacKinnon et al. | |
| 6,605,453 B2 * | 8/2003 | Ozkan et al. | 435/173.1 |
| 6,932,914 B2 * | 8/2005 | LeClair | 216/52 |
| 7,367,948 B2 | 5/2008 | O'Donnell et al. | |

OTHER PUBLICATIONS

Ishida et al; "Cavitation Bubble Behavior Near Solid Boundaries"; Proc. of the Fourth International Symposium on Cavitation,, 2001; 8 pages.*

Ishida et al; "Cavitation Bubble Behavior Near Solid Boundaries"; Proc. of the Fourth International Symposium on Cavitation, 2001; 8 pages.*

(Continued)

*Primary Examiner*—David Shay
(74) *Attorney, Agent, or Firm*—Brooks Kushman P.C.

(57) ABSTRACT

A method and system to create and acoustically manipulate without destroying a microbubble which, in biological applications, can manipulate structures such as cells and subcellular structures at a nanoscopic scale.

23 Claims, 4 Drawing Sheets

OTHER PUBLICATIONS

Wu et al "Acoustic Radiation Force on a small compressible shpere in a focussed beam"; J. Acoust Soc Am; 87(3) Mar. 1990, pp. 997-1003.*

Milas, Susanne M., et al., Acoustic Characterization of Microbubble Dynamics In Laser-Induced Optical Breakdown, IEEE Transactions on Ultrasonics, Ferroelectrics And Frequency Control, vol. 50, No. 5, May 2003, pp. 517-522.

Milas, Susanne M., et al., Acoustic Detection of Microbubble Formation Induced By Enhanced Optical Breakdown of Silver/Dendrimer Nanocomposites, Applied Physics Letters, vol. 82, No. 6, Feb. 10, 2003, pp. 994-996.

O'Donnell, M., et al., Acoustic Detection of Laser Induced Optical Breakdown In Dendrimer Nanocomposites: Implications For Site Targeted Molecular Diagnostics And Therapeutics, IEEE Ultrasonic Symposium, Oct. 8-11, 2002, pp. 1961-1964.

Tomita, Y., et al., Behavior of Laser-Induced Cavitation Bubbles in Liquid Nitrogen, Journal of Applied Physics, vol. 88, No. 10, Nov. 15, 2000, pp. 5593-6001.

Venugopalan, Vasan, et al., Role of Laser-Induced Plasma Formation in Pulsed Cellular Microsurgery and Micromanipulation, Physical Review Letter, vol. 88, No. 7, Feb. 18, 2002, pp. 078103-1-078103-4.i.

Noack, Joachim, et al., Influence of Pulse Duration on Mechanical Effects After Laser-Induced Breakdown in Water, Journal of Applied Physics, vol. 83, No. 12, Jun. 15, 1998, pp. 7488-7495.

Ye, Jing Yong, et al., Enhancement of Laser-Induced Optical Breakdown Using Metal/Dendrimer Nanocomposites, Applied Physics Letters, vol. 80, No. 10, Mar. 11, 2002, pp. 1713-1715.

Dayton, Paul A., et al., Optical And Acoustical Dynamics of Microbubble Contrast Agents Inside Neutrophils, Biophysical Journal, vol. 80, Mar. 2001, pp. 1547-1556.

File History of U.S. Appl. No. 10/643,659, filed Aug. 19, 2003.

* cited by examiner

FIGURE 6

120 — PROPAGATING AT LEAST ONE ULTRAFAST LASER PULSE TROUGH A MATERIAL TO CREATE A MICROBUBBLE WITHIN THE MATERIAL VIA LASER INDUCED OPTICAL BREAKDOWN (LIOB) WITH LITTLE OR NO CHANGE TO MATERIAL IMMEDIATELY ADJACENT TO THE MICROBUBBLE AND TO CREATE AT LEAST ONE ACOUSTIC SHOCK WAVE VIA LIOB WHEREIN THE AT LEAST ONE ACOUSTIC SHOCKWAVE OPERATES AS A HIGH FREQUENCY, HIGH PRECISION ACOUSTIC SOURCE

122 — PROPAGATING AT LEAST ONE ACOUSTIC WAVE THROUGH THE MATERIAL TO A SURFACE OF THE MICROBUBBLE TO CONTROLLABLY MANIPULATE THE MICROBUBBLE WITHIN THE MATERIAL WITHOUT CAUSING THE DESTRUCTION OF THE MICROBUBBLE

METHOD AND SYSTEM TO CREATE AND ACOUSTICALLY MANIPULATE A MICROBUBBLE

CROSS-REFERENCE TO RELATED APPLICATION

This application claims the benefit of U.S. provisional application Ser. No. 60/392,318, filed Jun. 26, 2002.

BACKGROUND OF THE INVENTION

1. Field of the Invention

This invention relates to methods and systems to create and acoustically manipulate a microbubble.

2. Background Art

Ultrafast lasers allow light to interact with materials in a femtosecond time period, with peak powers many orders of magnitude higher than that of continuous wave light but with low average powers. Interestingly, an optically transparent material that has no linear absorption of incident laser light may have strong nonlinear absorption under high intensity irradiation of a femtosecond pulsed laser. Nonlinear absorption can lead to photodisruption of the material by generating a fast, expanding high-temperature plasma. Measurable secondary affects of the plasma include shock wave emission, temperature increases and microbubble generation. Many applications of ultrafast laser-induced optical breakdown (LIOB) have been developed recently such as micromachining of solid materials, microsurgery of tissues, and high-density optical data storage.

The dominant breakdown attributes studied in liquids are shock wave emission and microbubble generation. As shock waves propagate spherically outward from the laser's focus, they dissipate energy and can be considered broadband pressure waves after propagating only a few wavelengths from the source.

Relatively long wavelength light in the near infrared can penetrate several mm of tissue. High intensity ultrafast pulses (typically several hundred fsec or less in duration) can be focused to internal structures, producing nonlinear photodisruption only in a very small region centered at the focal point of the optical system. Because of the short pulse duration, the total energy per pulse is very small, so there is virtually no damage outside of the photodisruption zone. Such procedures are used for non-invasive eye surgery at the micron scale, as shown in U.S. Pat. No. 6,146,375. Recent results have demonstrated that these methods can be extended to produce nanoincisions without any damage to surrounding tissue.

A concomitant of the photodisruption process is a nanobubble. These bubbles can remain in tissue for a period ranging from several msec to minutes, depending on the mechanical environment.

U.S. Pat. No. 6,391,020 discloses photodisruptive laser nucleation and ultrasonically-driven cavitation of tissues and materials.

"Optical tweezers," as described in U.S. Pat. Nos. 5,620,857 and 6,416,190, are used to manipulate biological structures such as individual macromolecules and subcellular structures. Optical tweezers require an optically refracting bead, limiting this approach to isolated preparations (i.e., individual molecules or cells or isolate systems).

SUMMARY OF THE INVENTION

An object of the present invention is to provide a method and system to create and acoustically manipulate without destroying a microbubble that does not require an external component such as a refractive bead.

While the preferred embodiment of the invention focuses on applications in cell and molecular biology, applications of the invention are not limited to this specific domain and may also include other applications where LIOB has been used.

In carrying out the above object and other objects of the present invention, a method to create and acoustically manipulate a microbubble within a volume of material is provided. The method includes propagating at least one laser pulse through the material to create a microbubble within the material. The method further includes propagating at least one acoustic wave through the material to a surface of the microbubble to controllably manipulate the microbubble within the material without destroying the microbubble.

The at least one laser pulse may be an ultrafast laser pulse, and the microbubble may be created via laser-induced optical breakdown (LIOB) with little or no change to material immediately adjacent to the microbubble.

The volume of material may include a liquid or semi-liquid material.

The at least one acoustic wave may include an ultrasound wave.

The ultrasound wave may exert a substantially continuous force or a pulsed force at the surface of the microbubble.

The at least one acoustic wave may exert a force in the nano-Newton to micro-Newton level at the surface of the microbubble.

The at least one acoustic wave may exert a force in the pico-Newton to femto-Newton level at the surface of the microbubble.

The step of propagating the at least one acoustic wave may cause the microbubble to exert a mechanical force on at least one structure in contact with the microbubble.

The at least one structure may be a biological structure.

The step of propagating the at least one acoustic wave may cause the microbubble to move within the volume of material.

The method may further include measuring elasticity of material in contact with the microbubble based on movement of the microbubble.

The step of propagating the at least one acoustic wave may cause the microbubble to mix the material.

The microbubble may be a nanobubble.

The step of propagating the at least one acoustic wave may cause the microbubble to manipulate at least one structure in contact with the microbubble.

The volume of material may be a cell culture or intact tissue.

The volume of material may be an extracellular medium of a diffuse cell culture, and the step of propagating the at least one acoustic wave may cause the microbubble to manipulate at least one cell for patterning.

The at least one laser pulse may be a femtosecond laser pulse.

The microbubble may have an optical refractive index different from an optical refractive index of the material, and the method may further comprise propagating a beam of light through the microbubble.

The step of propagating the at least one laser pulse may also create at least one acoustic shock wave via LIOB. The at least one acoustic shock wave may operate as a high frequency, high precision acoustic source.

Further in carrying out the above object and other objects of the present invention, a system to create and acoustically manipulate a microbubble within a volume of material is provided. The system includes a pulsed laser for generating at least one laser pulse. An optical subsystem directs the at least one laser pulse to the material wherein the at least one laser pulse propagates through the material to create a microbubble within the volume of material. An acoustic source directs acoustic energy to the material wherein at least one acoustic wave propagates through the material to a surface of the microbubble to controllably manipulate the microbubble within the volume of material without destroying the microbubble.

The microbubble may be created via laser-induced optical breakdown (LIOB) with little or no damage to material immediately adjacent to the microbubble.

The source may be an ultrasound source, an ultrasound wave may be propagated in a direction through the material, and the microbubble may move in the direction of the ultrasound wave.

The system may further include a modulated acoustic source for directing modulated acoustic energy to the material. At least one modulated acoustic wave may propagate through the material to the microbubble to cause the microbubble to mix material in a neighborhood of the microbubble.

The system may further include means for measuring elasticity of material in contact with the microbubble based on movement of the microbubble.

The above object and other objects, features, and advantages of the present invention are readily apparent from the following detailed description of the best mode for carrying out the invention when taken in connection with the accompanying drawings.

BRIEF DESCRIPTION OF THE DRAWINGS

FIG. 6 is a block diagram flow chart of another embodiment of a method of the present invention.

DETAILED DESCRIPTION OF THE PREFERRED EMBODIMENTS

In general, the present invention relates to a method and system to create and acoustically manipulate a microbubble without destroying the microbubble. In one embodiment, an incident ultrafast laser pulse is nonlinearly absorbed to produce a miocrobubble via photodisruption. For cell biology applications, a high numerical aperture (NA) lens tightly focuses the ultrafast pulse inside a cell of interest. Photodisruption at the focus will produce a microbubble representing a nearly ideal acoustic reflector. The microbubble can be manipulated with either continuous-wave or pulsed ultrasound sources of relative low frequency and long wavelength (for example, 1 MHz ultrasound representing a wavelength of about 1.5 mm in biological systems). At this frequency, ultrasonic absorption is minimal. However, the radiation force on the microbubble can be significant since it is an ideal acoustic reflector. Radiation forces at reasonable ultrasonic intensities can easily reach the nNewton-to-$\mu$Newton level at the microbubble surface. Very small radiation forces at the pNewton or fNewton levels can also be produced simply by reducing the ultrasonic intensity. Consequently, under remote control this approach can provide a wide dynamic range of forces to individual cells and subcellular components in contact with the microbubble.

Microbubbles in tissue have a finite lifetime. With the present invention, microbubbles are created with ultrafast optical pulses, manipulated with ultrasound, and then removed from the system over periods ranging from msec to minutes depending on the detailed mechanical environment of the microbubble. This feature overcomes many of the limitations of the prior art "optical tweezers."

The ability to place a microbubble anywhere in three dimensions within a cell culture or intact tissue, manipulate it with ultrasound in situ, and have it passively reabsorbed overcomes the primary limitations of "optical tweezers." For this reason, the technique of the present invention may be called "acoustic tweezers." This same technique can also be used to place microbubbles in the extracellular medium of a diffuse cell culture and manipulate cells with ultrasound for micro- and nanopatterning in highly controlled cell cultures.

Figure 1:
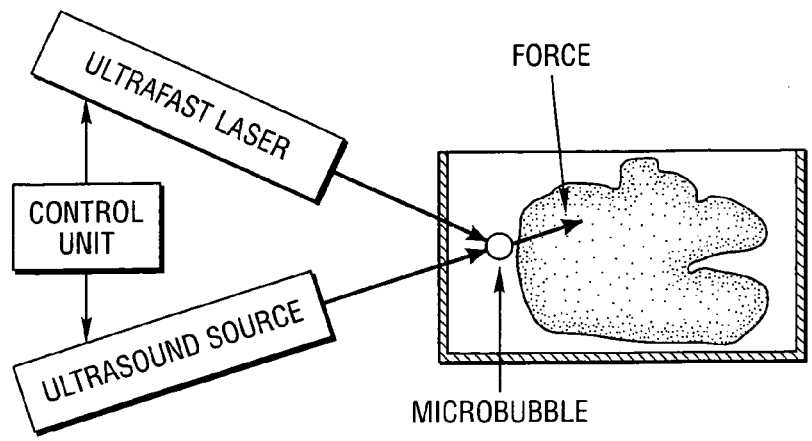
FIG. 1 is a schematic view of one embodiment of a system of the present invention.

FIG. 1 schematically discloses a well-controlled nanobubble inside biological tissue that can be used to exert precise forces on cells, or smaller structures, using ultrasound. Here, the microbubble is produced in the extracellular space of a tissue culture using a femtosecond laser pulse focused to this region. Synchronized with the optical system (i.e., ultrafast laser) by a control unit, an ultrasonic system (i.e., ultrasound source) insonifies the object immediately after the microbubble is created with a specified acoustic intensity to produce a specified radiation force on the microbubble. The microbubble will move in the direction of the ultrasound beam. In this way, a force of known magnitude and direction can be remotely applied to the cell. For example, the cell could be placed at a specific position as part of a biological micropatterning system. This use of a radiation force to produce precise mechanical forces is similar to optical tweezers. However, the acoustic system does not need a refractive optical bead—the active element is a fleeting nanobubble only present when forces need to be applied.

Figure 2:
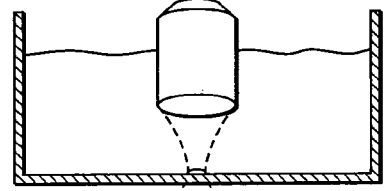
FIG. 2 is a schematic view of an experimental set-up with optical and acoustical alignment; laser pulses are focused at an inner surface of a tank bottom.
Figure 2:
Figure 2:

FIG. 2 schematically shows how microbubbles may be produced by laser-induced optical breakdown (LIOB) in water. Femtosecond laser pulses are focused by an optical element or lens just inside the surface of a small liquid tank. A tightly focused, high frequency, single-element ultrasonic transducer is positioned such that its focus coincides axially and laterally with this laser focus. When optical breakdown occurs, a microbubble forms and a pressure wave is emitted (i.e., acoustic emission).

Figure 3:
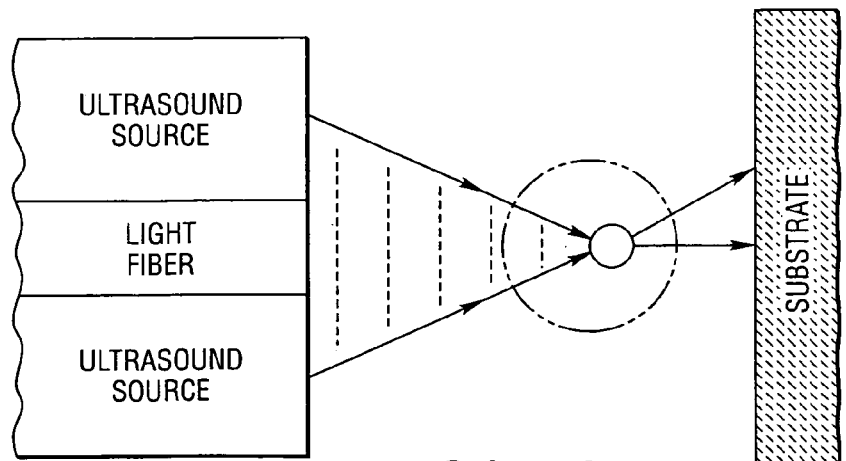
FIG. 3 is a schematic view of another embodiment of a system of the present invention.

FIG. 3 schematically shows a laser light fiber which is used to propagate one or more laser pulses within a medium (indicated by dashed vertical lines) to form a microbubble (the solid, small circle) and a shock wave (the dashed, larger circle). A pair of ultrasound sources positioned about the light fiber propagate acoustic energy in the form of acoustic waves in the medium to force the microbubble against a surface of a substrate or other structure such as for patterning.

One purpose of this invention is to provide a new method to remotely manipulate cells and subcellular structures within cell culture, and ultimately intact tissue. The method may use both ultrafast optics and ultrasonics to produce a system with equivalent control at nanoscopic dimensions that does not require an external component, such as a refractive bead. This means it can be applied to whole tissue culture, or even ultimately to intact tissue.

One advantage of the method and system of the invention is that it is non-contact (i.e., remotely controlled) and can be used within cell culture and intact tissue. It provides all the features of optical tweezers without requiring beads.

There are many other potential applications of this technology in both biological and non-biological systems. Anywhere "optical tweezers" have been applied, "acoustic tweezers" should have an advantage.

Four potential applications for "acoustic tweezers" are as follows:

1. Patterning—If a microbubble touches a surface, then when an acoustic wave pushes on the microbubble, fluid around the microbubble can move with a high velocity toward the surface. This effect is called acoustic microstreaming. By precisely positioning a laser-induced microbubble at the surface of a substrate, acoustic waves can force the fluid to interact with the substrate surface. This approach can be used for micro- and nanopatterning of the substrate surface.
2. The shock wave associated with microbubble creation (i.e., an acoustic shock wave is launched simultaneous with microbubble creation during a photodisruption event) can be used as a high frequency, high precision acoustic source.
3. Fluid mixing—If a microbubble is acoustically-levitated within a liquid, then a second, modulated acoustic source can be used for fluid mixing in the neighborhood of the microbubble. Since the microbubble can be placed anywhere in the fluid that the optical pulsed beam can propagate, one can effectively create a micromixer without constructing a device.
4. Optical tweezing—Because the microbubble has a much different optical refractive index compared to the surrounding fluid, the microbubble can also be used for optical manipulation as well as acoustic manipulation.

The present invention may also be used to measure tissue elastic properties using acoustic radiation force on laser-generated microbubbles. For example, an acoustic radiation force may be applied to microbubbles generated by laser-induced optical breakdown (LIOB) to study the mechanical response of the surrounding medium. The technique of applying acoustic radiation force to microbubbles seems well suited to monitor changes in intraocular lens elasticity during a potential presbyopia treatment involving LIOB. While traditional elasticity imaging and more recent techniques involving acoustic radiation force would be confounded by the limited speckle pattern in the lens, application of acoustic radiation force to microbubbles generated by LIOB would not have such limitations. Optical breakdown occurs when sufficiently high threshold fluence is attained at the focus of femtosecond pulsed lasers, including plasma formation and microbubble generation. LIOB microbubbles are of particular interest because they can be generated at very precise locations and optical parameters can be varied to control size.

Femtosecond laser pulses (700 fs) are focused in the volume of gelatin phantoms of varying concentration to form microbubbles. A two-element ultrasonic transducer generates acoustic radiation force on individual microbubbles while monitoring their displacement within an elastic medium. Gelatin phantoms with concentrations of 5%, 7.5% and 10% are used to compare the displacement of individual microbubbles in response to 1.5 MHz focused ultrasound by the outer element. Two types of acoustic excitation have been investigated: 1) single bursts ranging from 33 μsec to 200 ms; and 2) pulsed bursts at 1.22 kHz. The inner element receives pulse-echo recordings before, during and after the excitation bursts and correlation processing is performed to monitor microbubble position. Maximal microbubble displacements of 330 μm, 124 μm, and 48 μm have been measured in response to pulsed excitation in 5%, 7.5% and 10% gelatin phantoms, respectively. Alternatively, maximal microbubble displacements of 423 μm, 140 μm, and 60 μm have been measured in response to a single 6.7 ms ultrasound burst in 5%, 7.5% and 10% gelatin phantoms, respectively. These results demonstrate that microbubble displacement induced by acoustic radiation force is directly related to the gelatin concentration and, therefore, the elasticity of the surrounding medium.

Figure 4:
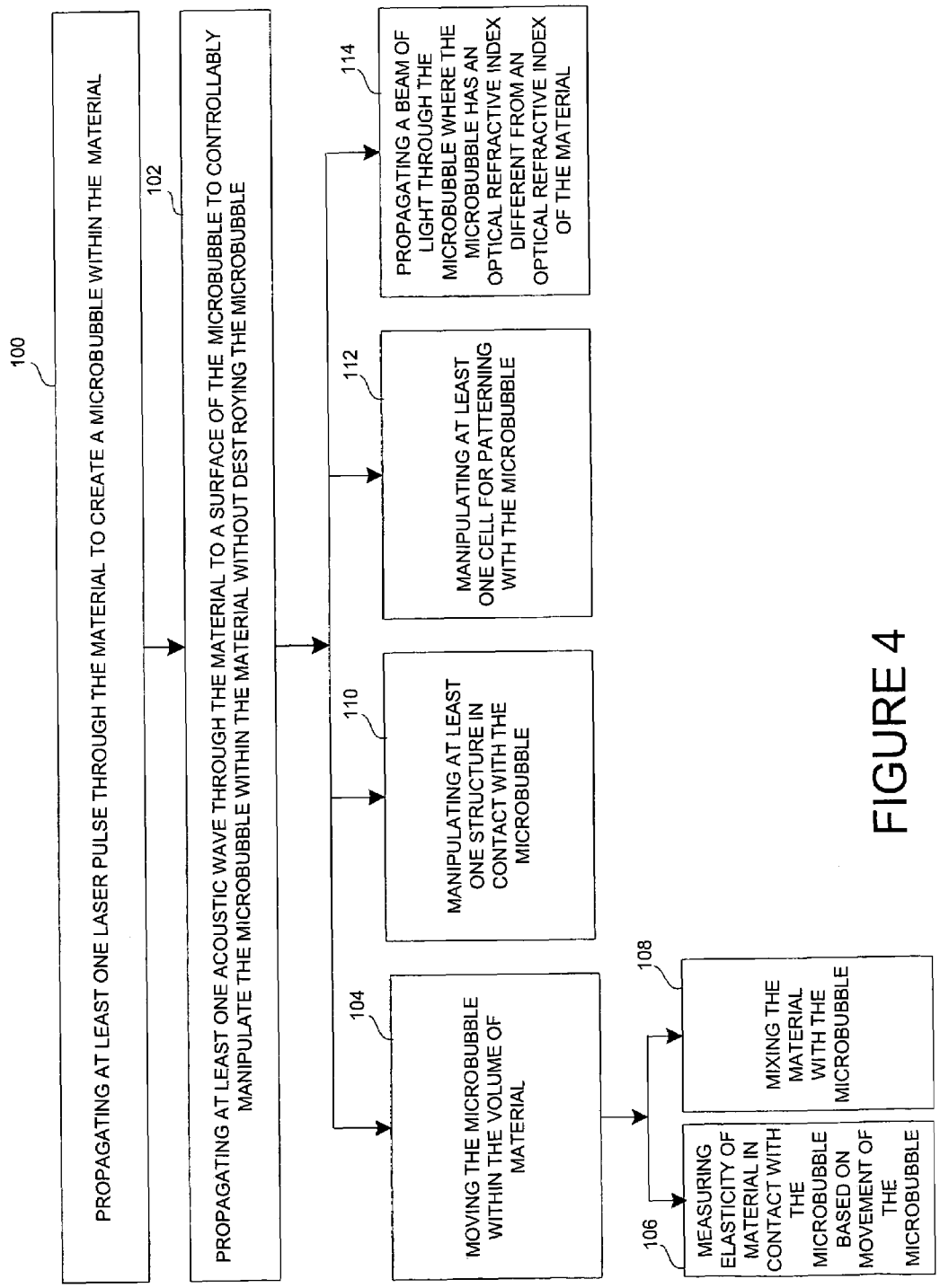
FIG. 4 is a block diagram flow chart of an embodiment of a method for the present invention.

FIG. 4 is a block diagram flow chart of an embodiment of a method of the present invention.

Figure 5:
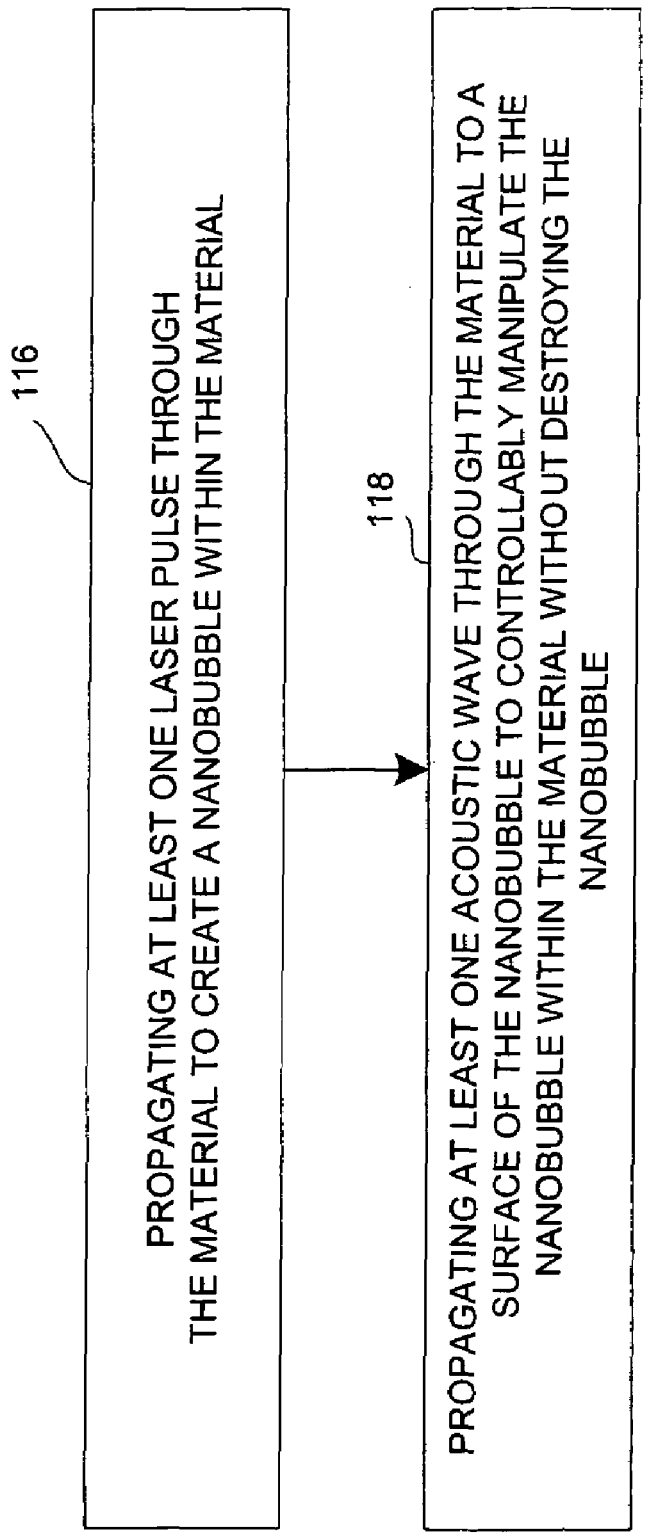
FIG. 5 is a block diagram flow chart of another embodiment of a method of the present invention.

FIG. 5 is a block diagram flow chart of another embodiment of a method of the present invention.

FIG. 6 is a block diagram flow chart of another embodiment of a method of the present invention.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A system to create and acoustically manipulate a microbubble within a volume of material, the system comprising:
   a pulsed laser for generating at least one laser pulse;
   an optical subsystem for directing the at least one laser pulse to the material wherein the at least one laser pulse propagates through the material to create a microbubble within the volume of material;
   an acoustic source for directing acoustic energy to the material wherein at least one acoustic wave propagates through the material to exert a radiation force at an exterior surface of the microbubble to controllably manipulate the microbubble and displace a central portion of the microbubble within the volume of material without causing the destruction of the microbubble; and
   an imaging subsystem measure elasticity of material in contact with the microbubble based on movement of the microbubble.

2. The system as claimed in claim 1, wherein the source is an ultrasound source and wherein an ultrasound wave is propagated in a direction through the material and wherein the microbubble moves in the direction of the ultrasound wave.

3. The system as claimed in claim 1, wherein the at least one acoustic wave includes an ultrasound wave.

4. The system as claimed in claim 3, wherein the ultrasound wave exerts a substantially continuous radiation force at the surface of the microbubble.

5. The system as claimed in claim 3, wherein the ultrasound wave exerts a pulsed radiation force at the surface of the microbubble.

6. The system as claimed in claim 1, wherein the microbubble is a nanobubble.

7. The system as claimed in claim 1, wherein the at least one laser pulse is a femtosecond laser pulse.

8. The system of claim 1 wherein the acoustic source is external to the material.

9. A method to create and acoustically manipulate a microbubble within a volume of material, the method comprising:
   propagating at least one laser pulse through the material to create a microbubble within the material;
   propagating at least one acoustic wave through the material to exert a radiation force at an exterior surface of the microbubble to controllably manipulate the microbubble and displace a central portion of the microbubble within the material without causing the destruction of the microbubble by the propagating of the at least one acoustic wave; and measuring elasticity of material in contact with the microbubble based on movement of the microbubble.

10. A method to create and acoustically manipulate a microbubble within a volume of material, the method comprising:

propagating at least one laser pulse through the material to create a microbubble within the material;

propagating at least one acoustic wave through the material to exert a radiation force at an exterior surface of the microbubble to controllably manipulate the microbubble and displace a central portion of the microbubble within the material without causing the destruction of the microbubble; and measuring elasticity of material in contact with the microbubble based on movement of the microbubble.

11. The method as claimed in claim 10, wherein the at least one laser pulse is an ultrafast laser pulse and wherein the microbubble is created via laser induced optical breakdown (LIOB) with little or no change to material immediately adjacent to the microbubble.

12. The method as claimed in claim 10, wherein the at least one acoustic wave exerts a radiation force between $1 \times 10^{-9}$ Newtons and $1 \times 10^{-6}$ Newtons at the surface of the microbubble.

13. The method as claimed in claim 10, wherein the at least one acoustic wave exerts a radiation force between $1 \times 10^{-12}$ Newtons and $1 \times 10^{-15}$ Newtons at the surface of the microbubble.

14. The method as claimed in claim 10, wherein the step of propagating the at least one acoustic wave causes the microbubble to mix the material.

15. The method as claimed in claim 10, wherein the microbubble is a nanobubble.

16. The method as claimed in claim 10, wherein the step of propagating the at least one acoustic wave causes the microbubble to manipulate at least one structure in contact with the microbubble.

17. The method as claimed in claim 10, wherein the at least one laser pulse is a femtosecond laser pulse.

18. The method as claimed in claim 10, wherein the microbubble has an optical refractive index different from an optical refractive index of the material and wherein the method further comprises propagating a beam of light through the microbubble.

19. The method as claimed in claim 11, wherein the step of propagating the at least one laser pulse also creates at least one acoustic shock wave via LIOB.

20. The method of claim 10 wherein the at least one acoustic wave is generated external to the material.

21. The method as claimed in claim 10, wherein the at least one acoustic wave includes an ultrasound wave.

22. The method as claimed in claim 21, wherein the ultrasound wave exerts a substantially continuous radiation force at the surface of the microbubble.

23. The method as claimed in claim 21, wherein the ultrasound wave exerts a pulsed radiation force at the surface of the microbubble.

* * * * *

UNITED STATES PATENT AND TRADEMARK OFFICE
CERTIFICATE OF CORRECTION

PATENT NO.         : 7,549,985 B2                                      Page 1 of 1
APPLICATION NO. : 10/603341
DATED              : June 23, 2009
INVENTOR(S)        : Matthew O'Donnell It is certified that error appears in the above-identified patent and that said Letters Patent is hereby corrected as shown below:

Column 6, Line 39, Claim 1:

After "subsystem" insert -- to --.

Signed and Sealed this

First Day of September, 2009

David J. Kappos
*Director of the United States Patent and Trademark Office*